United States Patent
Sebastián et al.

[11] Patent Number: 5,658,284
[45] Date of Patent: Aug. 19, 1997

[54] CONNECTION MEMBER FOR THE CONNECTION OF A RESILIENT ROD WITH A BONE SCREW WHICH CAN BE ANCHORED IN A VERTEBRA

[75] Inventors: D. César Sebastián; D. José Ignacio Abad, both of Malága, Spain; Mustafa Yurtsever, Cham; Nikolaus Baur, Flurlingen, both of Switzerland

[73] Assignee: Allo Pro AG, Baar, Switzerland

[21] Appl. No.: 497,163

[22] Filed: Jun. 30, 1995

[30] Foreign Application Priority Data

Jun. 30, 1995 [EP] European Pat. Off. ............ 94810388

[51] Int. Cl.$^6$ .................................................. A61B 17/56
[52] U.S. Cl. ........................... 606/61; 606/72; 606/73
[58] Field of Search ...................... 606/61, 72, 73

[56] References Cited

U.S. PATENT DOCUMENTS

| | | | |
|---|---|---|---|
| 5,002,542 | 3/1991 | Frigg | 606/61 |
| 5,005,562 | 4/1991 | Cotrel | 606/61 |
| 5,010,879 | 4/1991 | Moriya et al. | 606/61 |
| 5,030,220 | 7/1991 | Howland | 606/73 |
| 5,147,360 | 9/1992 | Dubousset | 606/61 |
| 5,312,404 | 5/1994 | Asher et al. | 606/61 |
| 5,487,744 | 1/1996 | Howland | 606/61 |
| 5,520,687 | 5/1996 | Howland | 606/61 |

FOREIGN PATENT DOCUMENTS

| | | |
|---|---|---|
| 0330881 A1 | 9/1989 | European Pat. Off. . |
| 0384001 | 8/1990 | European Pat. Off. . |
| 0468264 A1 | 1/1992 | European Pat. Off. . |
| 046930 A1 | 2/1992 | European Pat. Off. . |
| 41 10002 | 5/1992 | Germany . |

*Primary Examiner*—Michael Buiz
*Assistant Examiner*—Julian W. Woo
*Attorney, Agent, or Firm*—Townsend and Townsend and Crew LLP

[57] ABSTRACT

A connection member for the connection of a resilient rod with a bone screw that can be anchored in a vertebra. The connection member comprises a fastener that acts on the rod, an accommodation part and a connection part. The accommodation part has a first opening for the accommodation of the rod. The first opening has a substantially round inner boundary surface formed from several partial surfaces with at least three different radii of curvature such that upon connection of the connection member with the resilient rod, the connection member has at least three regions of contact with the resilient rod at least three distinct and noncontiguous points.

16 Claims, 4 Drawing Sheets

CONNECTION MEMBER FOR THE CONNECTION OF A RESILIENT ROD WITH A BONE SCREW WHICH CAN BE ANCHORED IN A VERTEBRA

BACKGROUND OF THE INVENTION

1. Technical Field

The invention relates to a connection member for the connection of a resilient rod with a bone screw which can be anchored in a vertebra, and further to a device comprising such a connection member for the connection of at least two vertebrae.

2. Description of the Prior Art

It is known in the case of deformed or degenerated spinal columns to operatively clamp a correcting device via connection members to at least two vertebrae of a spinal column in order to thus give the spinal column a greater stability.

From EP 0384001 A1 a correcting device is known which clamps an elongated, resilient rod to a plurality of vertebrae of a spinal column with connection members. This device has a connection member with an opening for the accommodation of a part of an elongated rod. The connection member has a further connection region in order to clamp the connection member to a vertebra via bone screws. In one embodiment, the connection member has a screw with which the elongated rod is clampable within the connection member. This connection member has the disadvantage that when large forces act, a relative movement can result between the connection member and the resilient rod.

SUMMARY OF THE INVENTION

The advantages of the invention are that the connection member has a recess for the accommodation of an elongated rod, with the inner surface of the recess being formed such that only partial regions of the inner surface engage with the rod in an operative connection. The rod can have a cross-sectional area such as round, oval, elliptical, triangular or polygonal, so that the recess of the connection member is adapted to the cross-sectional area of the rod, such that only partial regions of the inner surface of the recess engage with the rod in an operative connection. A rod that is clamped in such a way with a screw within the connection member tends not to move relative to the connection member. The inner surface can have groove-shaped recesses for example extending in the longitudinal and/or transverse direction of the inserted rod. Furthermore, the surface of the rod can have groove-shaped recesses. Another embodiment that reduces the contact area between the rod and the inner surface of the recess involves the recess having inner boundary surface comprising a plurality of curved partial surfaces with at least three different radii of curvature. These radii of curvature can be larger or smaller than a radius of curvature of the rod, so that line-shaped contact surfaces result between the recess and the rod. It is particularly advantageous to realize a three-point mounting, wherein the rod is contacted at two line-shaped contact surfaces at the inner boundary surface, and the third point of mounting is provided by a connection means acting on the rod, such as a screw.

A further advantage of the invention is that more than one screw can be arranged in the connection member along the recess for the clamping of the rod, which affords the rod a particularly rigid support.

DETAILED DESCRIPTION OF THE PREFERRED EXEMPLARY EMBODIMENTS

Figure 1A:
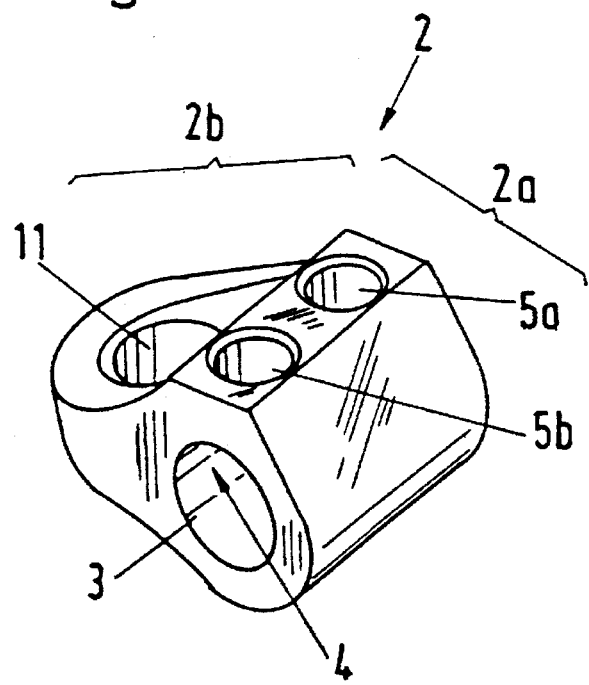
FIGS. 1a–1c are perspective views of embodiments of a connection member made in accordance with the present invention.

FIG. 1a shows a connection member 2 comprising an accommodation part 2a and a connection part 2b. The accommodation part 2a has a continuous opening 3 into which a rod 1 can be inserted which is connectable with the accommodation part 2a via connection means 6a, 6b which can be inserted into the recess 5a, 5b. The opening 3 has an inner boundary surface 4. The connection part 2b has an opening 11 through which a bone screw 8 is insertable in order to anchor the connection part 2b to a vertebra 7 of a spinal column.

Figure 1B:
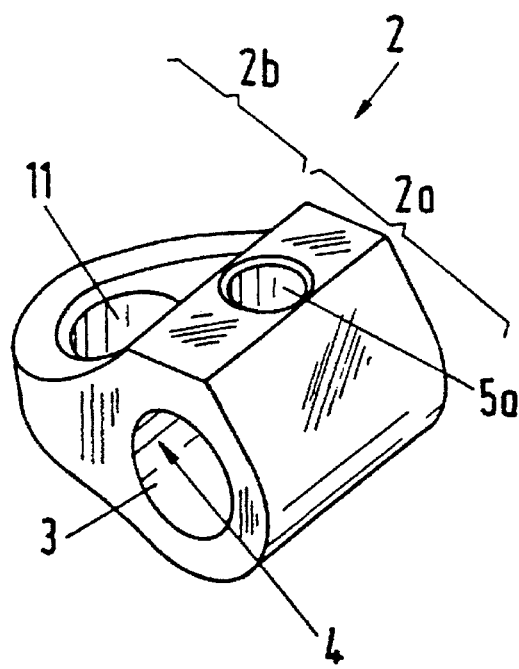

In FIG. 1b a further embodiment of a connection member 2 is shown which is formed in a similar manner as the embodiment illustrated in FIG. 1a. However, the embodiment illustrated in FIG. 1b only has one recess 5a for the accommodation of a connection means 6a.

Figure 1C:
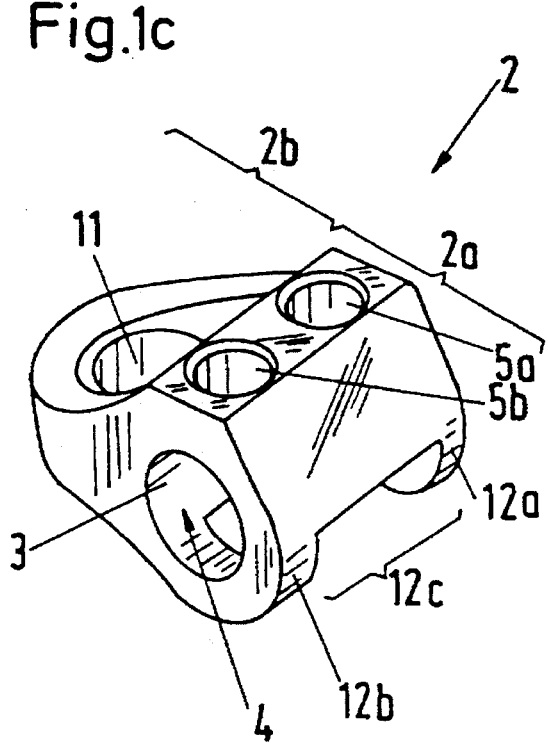
Figure 1D:
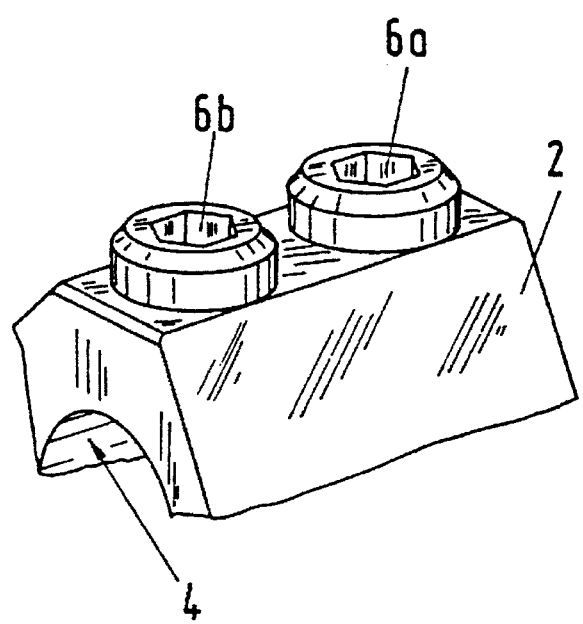
FIG. 1d is a detailed view of the fastener means of a connection member made in accordance with the present invention.
Figure 4:
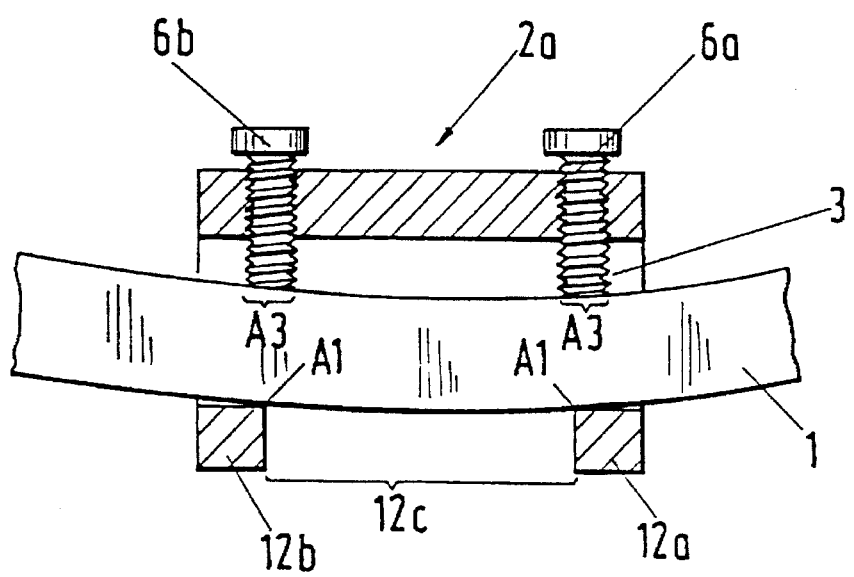
FIG. 4 is a longitudinal sectional view through the connection member illustrated in FIG. 1c.

Compared to the embodiment illustrated in FIG. 1a, the connection member 2 illustrated in FIG. 1c has an opening 12c in the inner boundary surface 4 which is opposite to the openings of the recess 5a, 5b and which extends in the longitudinal direction of the opening 3. Thus, two contact parts 12a, 12b are formed. FIG. 4 shows a longitudinal section through an accommodation part 2a where the extent of the opening 12c which is bounded on both sides by the contact parts 12a, 12b can be seen. An advantage of the indicated embodiment is that two contact regions A1 result, in particular for a curved rod, 1 when the rod 1 is pressed against the contact parts 12a, 12b by the fastener means 6a, 6b which act on the contact regions A3. The cross-section of the recess 3 is formed in a round manner in FIG. 4 so that the contact regions A1 are opposite to the fastener means 6a, 6b. If the cross-section of the recess 3 were, for example, formed in an oval or in an elliptical manner, then contact regions A1 would result which, as shown in FIG. 2d with A1, A2, could be arranged at the sides. If the curved rod 1 were to be inserted into a connection member of FIG. 1a, but with a round recess, then only one contact region A1 would result approximately in the center of the longitudinal extent of the opening or aperture 3.

Figure 2A:
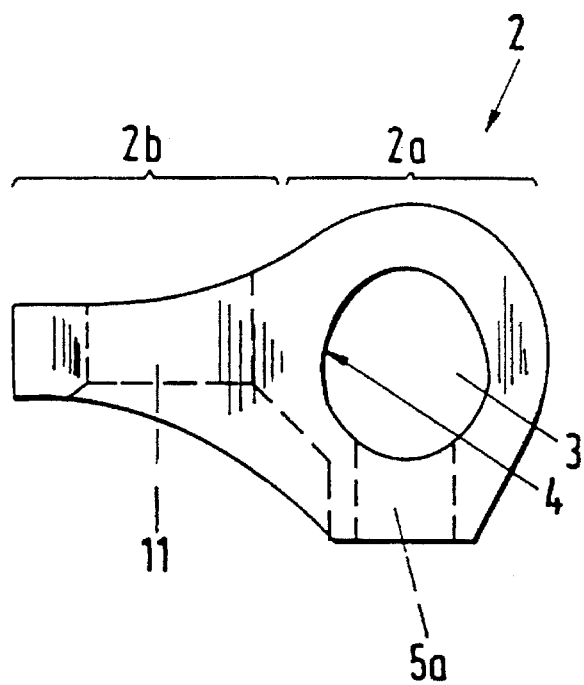
FIG. 2a is a side view of a connection member made in accordance with the present invention.

FIG. 2a shows a side view of a connection member 2 comprising an accommodation part 2a and a connection part 2b with an opening 11 and a recess 5a. The inner boundary surface 4 of the opening is essentially formed in a round manner, however not in a circular manner. From FIG. 2c it can be seen that the inner boundary surface 4 comprises a plurality of curved partial surfaces 4a, 4b, 4c having three different radii of curvature r1, r2, r3, so that in the present embodiment, an egg-shaped shape of the inner boundary surface 4 results. If the radius of curvature r3 of the partial surface 4c disposed opposite to the outlet opening of the recess 5a is chosen to be smaller than the radius of curvature R1 of the rod 1, then, as shown in FIG. 2d, two contact regions A1, A2 extending in the longitudinal direction of the opening 3 result, and thus a three-point contact of the rod 1 results together with the contact region A3 of the fastener means 6a. The shape of the inner boundary surface 4 of FIG. 2a, can, for example, also be formed in a round, an oval or an elliptical manner.

Figure 2B:
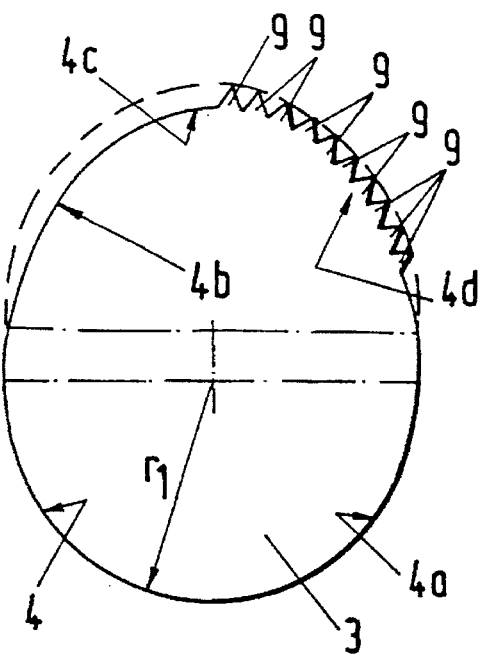
FIG. 2b is an elevational view illustrating the shape of the inner boundary surface with groove-shaped recesses.
Figure 2C:
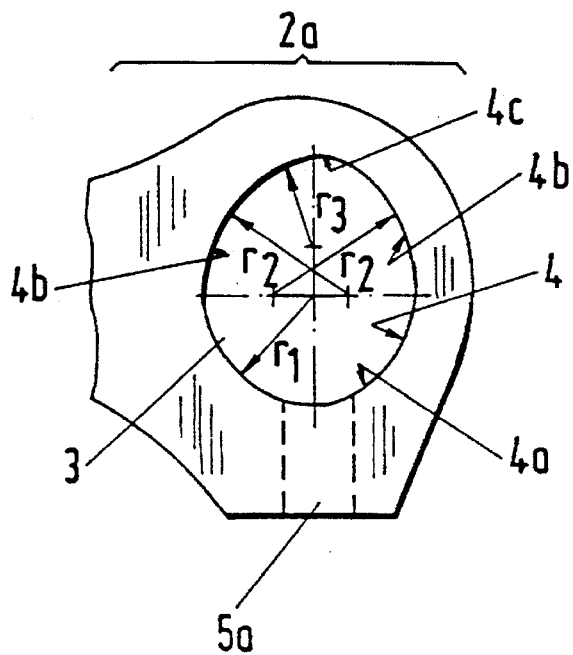
FIG. 2c is an elevational view illustrating the shape of the inner boundary surface.
Figure 2D:
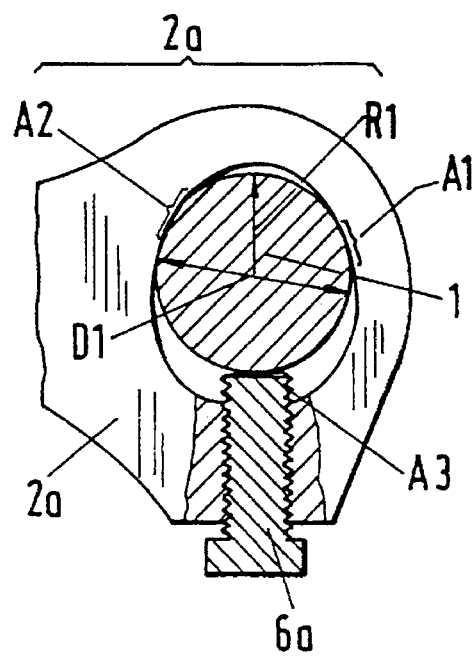
FIG. 2d is an elevational view with portions in cross-section illustrating a rod which is clamped in the connection member.
Figure 5:
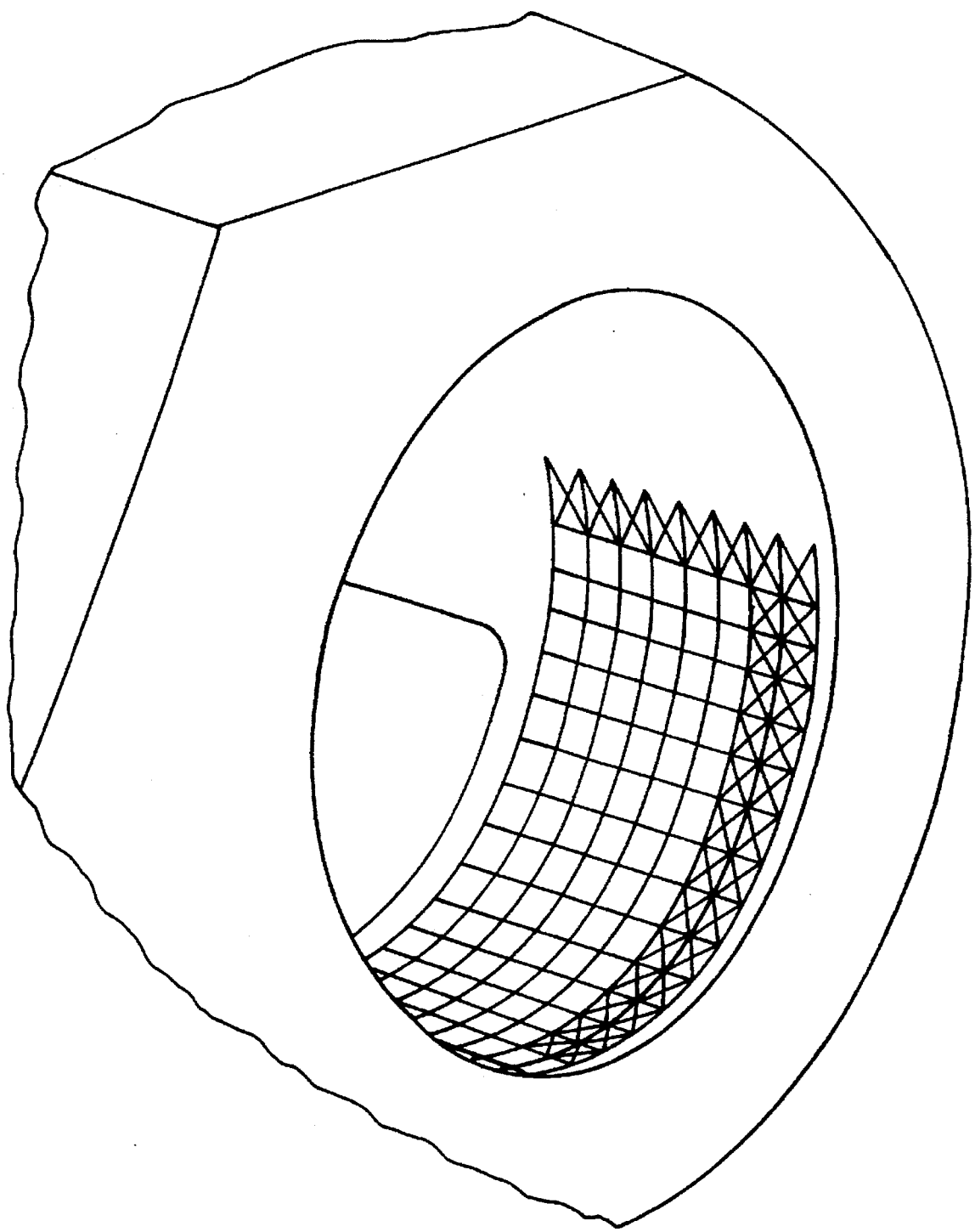
FIG. 5 is a perspective view of a portion of a connection member illustrating the inner boundary surface with a plurality of pyramidal elevations.

FIG. 2b shows a further embodiment of a shape of an inner boundary surface 4 comprising curved partial surfaces 4b, 4c, 4d with different radii of curvature. In addition, the partial surface 4d has groove-shaped recesses 9 extending in the longitudinal direction of the opening 3. This arrangement of the boundary surface 4d reduces the contact surface to the rod 1 and thereby a greater force per unit of area results, which allows the transfer of a larger force between the connection member 2 and the rod 1. Every form of an inner boundary surface 4, and thus also a round or elliptically formed boundary surface 4, can have groove-like recesses 9 extending, for example, in the longitudinal direction of the opening 3 and/or in the transverse direction of the opening 3, or in a different direction. An advantageous embodiment of the surface structure of the boundary surface 4 can be achieved by a plurality of pyramidal elevations as illustrated in FIG. 5. In the same way, it can be advantageous to provide the rod 1 with a surface structure, for example with a certain roughness as is achieved by for example sandblasting, or for example with groove-shaped recesses. The inner boundary surface 4 of FIG. 2b can also, however, comprise one or a plurality of partial surfaces 4a, 4b, 4c, 4d which have no curvature, i.e. which are formed in a flat manner. Even with this measure, the contact surface between the rod 1 and the boundary surface 4 can be reduced, wherein a level partial surface 4a, 4b, 4c, 4d can also have recesses such as grooves.

Figure 3:
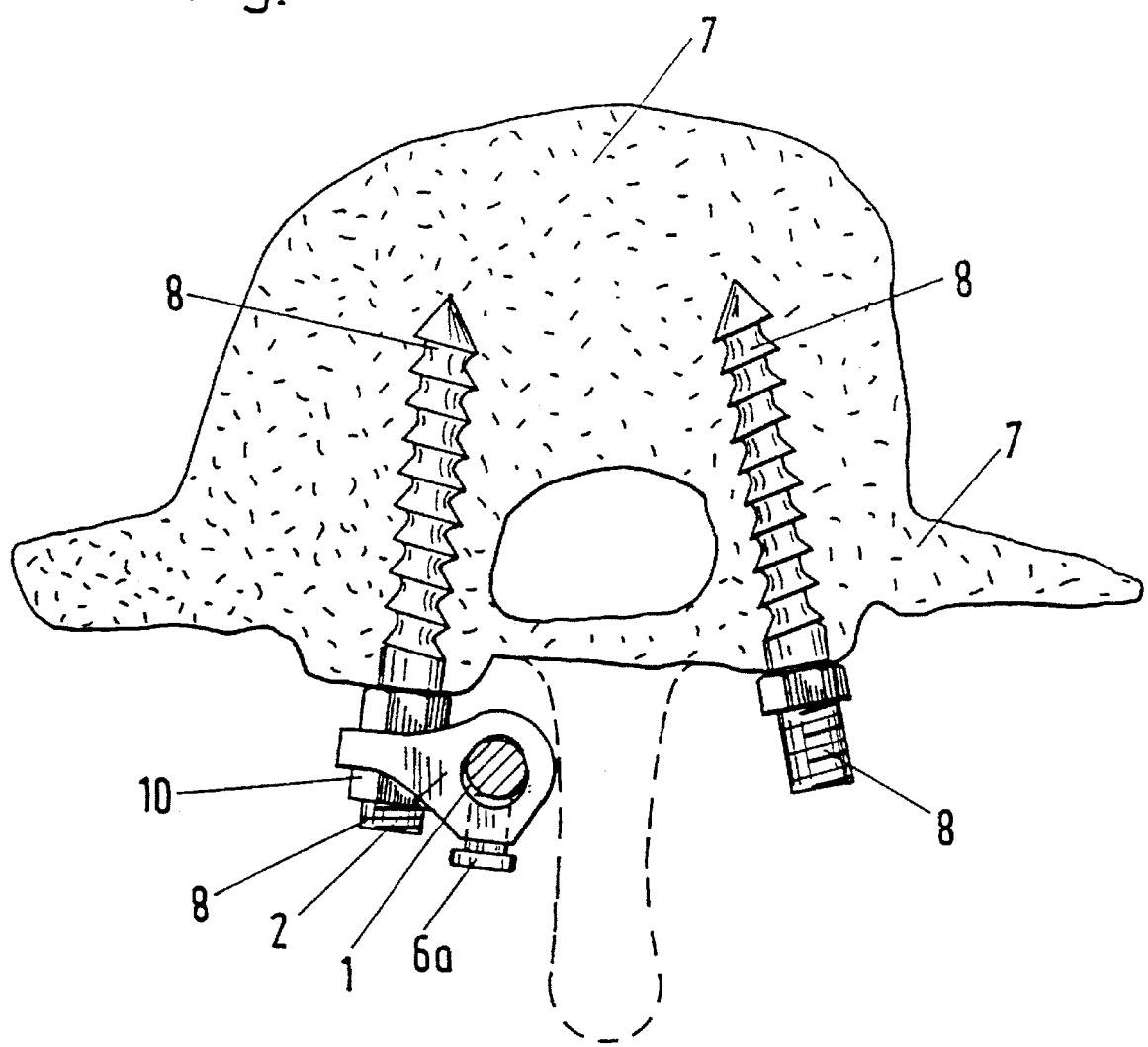
FIG. 3 is a cross-sectional view through a vertebra illustrating use of the connection member.

FIG. 3 shows a device for the connection of at least two vertebrae with a resilient rod 1. Fixing elements 8, such as bone screws, are anchored in the vertebra 7 and a connection member 2 is secured to the fixing or anchoring element 8 via a clamp nut 10. The resilient rod 1 is secured to the connection member 2 via a fastener means 6a.

What is claimed is:

1. A connection member for the connection of a resilient rod with a bone screw that can be anchored in a vertebra; the connection member comprising fastener means that act on the rod, an accommodation part and a connection part, the accommodation part having a first opening for the accommodation of the rod; wherein the first opening has a substantially round inner boundary surface formed from several curved partial surfaces with at least three different radii of curvature such that upon connection of the connection member with the resilient rod, the connection member has at least three regions of contact with the resilient rod at at least three distinct and non-contiguous locations.

2. The connection member of claim 1 wherein the inner boundary surface has groove-shaped recesses in order to reduce the contact surface between the accommodation part and the rod.

3. The connection member of claim 2 wherein the groove-shaped recesses cross one another.

4. The connection member of claim 3 wherein the groove-shaped recesses are arranged such that they mutually cross approximately perpendicularly and thereby the inner boundary surface has a plurality of pyramidal elevations.

5. The connection member of claim 1 wherein a surface of the rod has groove-shaped recesses in order to reduce the contact surface between the accommodation part and the rod.

6. The connection member of claim 5 wherein the inner boundary surface has groove-shaped recesses in order to reduce the contact surface between the accommodation part and the rod.

7. The connection member of claim 1 wherein the accommodation part has a recess for receiving the fastener means, and wherein a partial surface that is opposite the recess has a radius of curvature that is smaller than a radius of curvature of the rod.

8. The connection member of claim 7 wherein the remaining partial surfaces have a radius of curvature that is larger than the radius of curvature of the rod such that the rod is contacted by at least two contact regions at the inner boundary surface and by a contact region of the fastener means when the rod is engaged by the fastener means.

9. The connection member of claim 7 wherein the accommodation part has at least one further recess for receiving fastener means that act on the rod.

10. The connection member of claim 9 wherein the recesses for receiving fastener means are spaced apart in an axial direction with reference to the first opening.

11. The connection member of claim 9 wherein the accommodation part has a second opening that is opposite the recesses for receiving fastener means, the second opening being limited by two contact parts in the axial direction with reference to the first opening.

12. The connection member of claim 1 wherein the inner boundary surface has a substantially elliptical shape.

13. The connection member of claim 1 wherein the inner boundary surface has a substantially egg-shaped shape.

14. A device for the connection of at least two vertebrae comprising at least two connection members; bone screws for the anchoring of the at least two connection members in the vertebrae; and at least one rod for connecting the at least two connecting members; wherein each of the at least two connecting members comprises fastener means that act on the rod, an accommodation part and a connection part, the accommodation part having a first opening for the accommodation of the rod; wherein the first opening has a substantially round inner boundary surface formed from several curved partial surfaces with at least three different radii of curvature such that upon connection of the connection member with the resilient rod, the connection member has at least three regions of contact with the resilient rod at at least three distinct and non-contiguous spaced locations.

15. The device of claim 14 wherein the rod has a cross-sectional shape from the group of shapes consisting of round, oval, elliptical or polygonal.

16. The device of claim 14 wherein the accommodation part further comprises two recesses for receiving fastener means and a second opening that is opposite the two recesses for receiving fastener means, the second opening being limited by two contact parts in the axial direction with reference to the first opening.

* * * * *